United States Patent [19]

Mannweiler et al.

[11] Patent Number: 5,508,196
[45] Date of Patent: Apr. 16, 1996

[54] METHOD OF CONTINUOUSLY PREPARING A STERILE CULTURE MEDIUM

[75] Inventors: Klaus Mannweiler, Oelde; Ralf Kuchenbecker, Witten; Werner Rosenthal, Hemer, all of Germany

[73] Assignee: Westfalia Separator AG, Oelde, Germany

[21] Appl. No.: 302,715

[22] PCT Filed: May 7, 1993

[86] PCT No.: PCT/EP93/01118

§ 371 Date: Jul. 11, 1994

§ 102(e) Date: Jul. 11, 1994

[87] PCT Pub. No.: WO93/23525

PCT Pub. Date: Nov. 25, 1993

[30] Foreign Application Priority Data

May 9, 1992 [DE] Germany .......................... 42 15 339.5

[51] Int. Cl.$^6$ .......................... C12M 3/10; C12M 1/12; B01D 33/00
[52] U.S. Cl. .......................... 435/289.1; 210/650; 210/651; 210/653; 210/654; 210/655; 210/788; 422/93; 435/297.1
[58] Field of Search .................... 210/650, 651, 210/653, 654, 655, 788; 422/93; 439/287, 311

[56] References Cited

U.S. PATENT DOCUMENTS

| 4,832,851 | 5/1989 | Bowers et al. | 210/650 |
| 5,174,900 | 12/1992 | Nichols | 210/651 |

OTHER PUBLICATIONS

Lavsen et al. Biotechnology and Bioengineering vol. XVIII pp. 1433–1443 (1976).

Primary Examiner—Donald E. Czaja
Assistant Examiner—Jane Williams
Attorney, Agent, or Firm—Sprung Horn Kramer & Woods

[57] ABSTRACT

A method for continuously preparing a sterile culture medium comprises combining separate unsterilized fluid components in separate streams into a single mainstream. The mainstream is applied to a transverse flow filtration module having a membrane which separates the mainstream into a permeate and a retentate. The permeate is fed to a bioreactor and the retentate is diverted to a centrifuge to precipitate contaminants. The clarified retentate is returned into the mainstream upstream of the transverse flow filtration module.

9 Claims, 1 Drawing Sheet

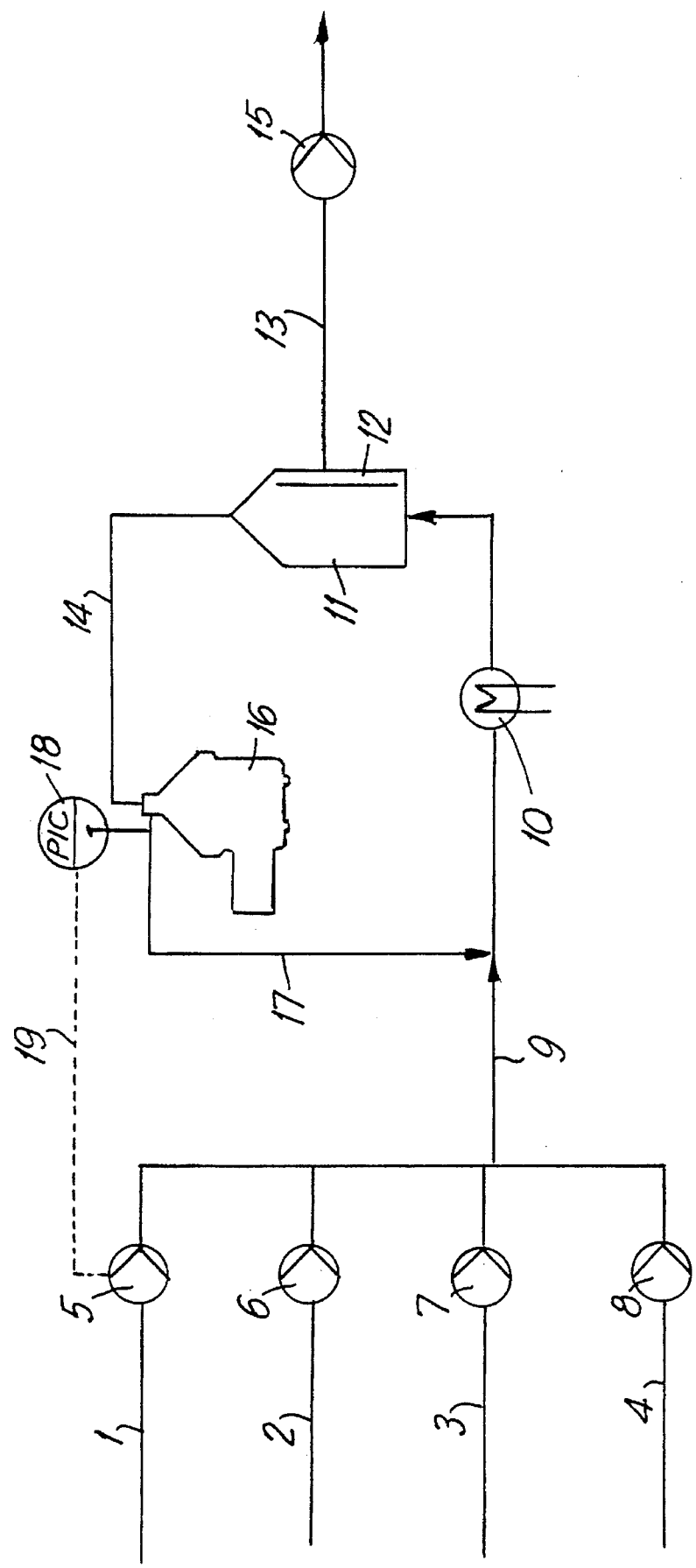

5,508,196

METHOD OF CONTINUOUSLY PREPARING A STERILE CULTURE MEDIUM

The invention concerns a method of continuously preparing a sterile culture medium, wherein various components are combined into a single mainstream appropriate for charging a bioengineering reactor.

The processing-technology stages in a continuous-operation bioengineering reactor essentially comprise culture-medium sterilization, fermentation, and product finishing or product analysis. Successful continuous operation of such a reactor depends on the quality of the incoming sterile medium among other factors. Three methods of preparing it are known, specifically high-temperature short residence time (HTSRT), filtering it sterile, and the use of contaminant-insensitive media.

In HTSRT the flowing non-sterile medium is heated in a heat exchanger to approximately 135° and maintained at that temperature for a few minutes. Any microorganisms are exterminated, and the result is a sterile culture medium. Although it exterminates germs very effectively, there are drawbacks to the method. Various components of the media tend to interact, sugar molecules and amino acids into melanoids for example. Again, some components, vitamins for example, are destroyed by heat.

In filtering sterile, the filter is interposed in the line leading to the reactor and the medium arrives sterile. Since this approach does not involve heat, the quality of the resulting medium is high. When several media are sterilized with the same filter, however, the device will clog up rapidly and becomes unreliable. This approach is accordingly employed fairly infrequently.

Contamination-insensitive components automatically result in a sterile culture medium because they by their very nature do not allow contaminants to proliferate. The only appropriate applications, however, are fermentation processes that occur in a highly acidic milieu or include antibiotics in the culture medium. The use of such procedures is limited.

The object of the present application is a method of continuously preparing a sterile culture medium that can be universally employed, will allow long-term continuous operation, and ensures careful treatment of the culture media.

This object is attained in accordance with the present invention as will now be described. The components arrive in tributaries. The still unsterilized components are combined into a mainstream. The mainstream is forwarded to a transverse-flow filtration module. The module accommodates a membrane that separates the mainstream into a permeate and a retentate. The permeate is forwarded to the reactor. The retentate is diverted to a centrifuge that precipitates any germs. The centrifuged retentate is returned to the mainstream flowing toward the filtration module.

The various components can accordingly be combined in accordance with the present invention even before they are sterilized, which simplifies management and increases flexibility with respect to combining various components. The centrifuge continuously centrifuges microorganisms out of the retentate lines and prevents them from proliferating on or in the membrane. The centrifuge also automatically maintains a high rate of recirculation, which also inhibits the growth of microorganisms on the membrane. Finally, the centrifuge ensures adequate pressure on the membrane.

The mainstream is maintained at a temperature of at least 70° C. by a heat exchanger once the retentate has been returned in one advantageous embodiment of the method. This procedure exterminates many germs and inhibits the growth of heat-resistant types, preventing overload of the centrifuge and filtration module. This temperature, however, is not high enough to damage the components of the media.

The diameters of the pores in the filter membrane in another advantageous embodiment of the method are 0.2 μm or less. This dimension has been demonstrated to allow rapid permeate flow while maintaining the sterilizing capability of the module. The best results have been obtained with pores 0.14 μm in diameter.

To prolong the life of the filtration module, the retentate should flow at least precisely as rapidly as the permeate. The retentate should preferably flow at least four times as rapidly as the permeate.

The flow of media components can be regulated with displacement pumps. Displacement pumps particularly facilitate the overall controls.

The pressure downstream of the centrifuge can be maintained constant by regulating the flow of one component of the media.

The flow of the other components of the media can then be adjusted to the regulated flow.

BRIEF DESCRIPTION OF THE DRAWING

The drawing depicts the flow of media through the reactor.

One embodiment of the present invention will now be specified with reference to the drawing, which comprises a single figure.

Displacement pumps 5, 6, 7, and 8 combine various component tributaries 1, 2, 3, and 4 into a mainstream 9. Mainstream 9 is heated in a heat exchanger 10 and then flows through a transverse-flow filtration module 11. Module 11 accommodates a membrane 12. Membrane 12 separates mainstream 9 into an accordingly sterilized permeate 13 and a non-sterile retentate 14. A pump 15 forwards permeate 13 to an unillustrated bioengineering reactor. Retentate 14 is diverted to a centrifuge 16. Centrifuge 16 constantly precipitates microorganisms out of retentate 14. The clarified retentate 17 leaving centrifuge 16 is returned to mainstream 9 before it enters heat exchanger 10. The line that conveys clarified retentate 17 accommodates a pressure regulator 18. Pressure regulator 18 communicates with displacement pump 5 through a line 19.

Displacement pumps 5, 6, 7, and 8 combine prescribed portions of tributaries 1, 2, 3, and 4 into mainstream 9 in the unsterilized section. This feature simplifies management of the plant and ensures extensive flexibility in the combination of various components.

Increasing the temperature of mainstream 9 to 70° C. in heat exchanger 10 exterminates many germs and inhibits the growth of heat-resistent types to such an extent that it prevents overload of the centrifuge and filtration module. The medium, however, never becomes hot enough to threaten its components.

The membrane 12 in transverse-flow filtration module 11 now separates the accordingly treated mainstream 9 into a sterile permeate 13 and a germy retentate 14. Retentate 14 must flow rapidly enough to prevent membrane 12 from clogging up.

Microorganisms are constantly precipitated out of retentate 14 in centrifuge 16 before the clarified retentate 17 is returned to mainstream 9 before it enters heat exchanger 10. The risk of microorganisms settling in or on the membrane is avoided. Centrifuge 16 also automatically maintains the rate of recirculation high enough to inhibit the growth of microorganisms on the membrane. Finally, the centrifuge ensures adequate pressure on the membrane.

It is practical for the pores in the membrane to be 0.14 μm in diameter. This ensures satisfactory throughput and sterilization on the part of the membrane.

The output from centrifuge 16 is maintained constant due to maintenance of the pressure downstream by a pressure regulator 18, which controls the displacement pump 5 that forward tributary 1.

Tributary 1 contributes a major portion of mainstream 9. The contributions of tributaries 2, 3, 4 are adjusted to that of tributary 1 by varying the output of pumps 6, 7, and 8 with an unillustrated regulator.

It is advantageous for centrifuge 16 to be a disk-type separator accommodating a device for diverting the clarified phase under pressure. The precipitated germs settle in the centrifuge and must be removed manually or, if the machine is self-emptying, automatically.

We claim:

1. A method for continuously preparing a sterile culture medium, comprising the steps of:

providing unsterilized fluid components in separate streams;

combining the separate streams into a single mainstream;

continuously applying the mainstream to a transverse flow filtration module having a membrane which separates the mainstream into a permeate and a retentate;

continuously feeding the permeate to a bioreactor;

diverting the retentate to a centrifuge to continuously precipitate contaminants out of the retentate; and returning clarified retentate from the centrifuge into the mainstream upstream of the transverse flow filtration module.

2. The method according to claim 1, further comprising maintaining the mainstream with the returned retentate at a temperature of at least 70° C.

3. The method according to claim 1, further comprising providing the membrane with pores having a diameter of no greater than 0.2 μm.

4. The method according to claim 1, further comprising providing the membrane with pores having a diameter of 0.14 μm.

5. The method according to claim 1, wherein the retentate flows through the transverse flow filtration module at a flow rate at least as great as a flow rate of the permeate.

6. The method according to claim 1, wherein the retentate flows though the transverse flow filtration module at a flow rate four times as great as a flow rate of the permeate.

7. The method according to claim 1, further comprising regulating the flow of the components in the separate streams with pumps.

8. The method according to claim 1, further comprising maintaining a constant pressure downstream of the centrifuge by regulating the flow of one of the components.

9. The method according to claim 8, wherein the step of maintaining a constant pressure further comprises adjusting the flow of other components to the flow of said one component.

* * * * *